US010076425B2

(12) United States Patent
Farina et al.

(10) Patent No.: US 10,076,425 B2
(45) Date of Patent: Sep. 18, 2018

(54) CONTROL OF LIMB DEVICE

(71) Applicants: Georg-August-Universitaet Goettingen Stiftung Oeffentlichen Rechts, Universitaetsmedzin, Goettingen (DE); Otto Bock HealthCare GmbH, Duderstadt (DE)

(72) Inventors: Dario Farina, Goettingen (DE); Dejan Popovic, Belgrade (RS); Bernhard Graimann, Obernfeld (DE); Marko Markovic, Goettingen (DE); Strahinja Dosen, Goettingen (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 15/598,975

(22) Filed: May 18, 2017

(65) Prior Publication Data

US 2017/0266019 A1 Sep. 21, 2017

Related U.S. Application Data

(63) Continuation of application No. 14/303,229, filed on Jun. 12, 2014, now abandoned.

(30) Foreign Application Priority Data

Jun. 12, 2013 (EP) ..................... 13171671

(51) Int. Cl.
*A61F 2/68* (2006.01)
*A61F 2/54* (2006.01)
(Continued)

(52) U.S. Cl.
CPC ............... *A61F 2/54* (2013.01); *A61F 2/583* (2013.01); *A61F 2/68* (2013.01); *A61F 2/72* (2013.01);
(Continued)

(58) Field of Classification Search
CPC ...... A61F 2/54; A61F 2/68; A61F 2/72; B25J 9/1612; G05B 2219/45172
See application file for complete search history.

(56) References Cited

U.S. PATENT DOCUMENTS 4,650,492 A 3/1987 Barkhordar et al.
6,244,873 B1 6/2001 Hill et al.
(Continued)

FOREIGN PATENT DOCUMENTS

WO 2008/098072 A2 8/2008
WO 2011/022572 A1 2/2011

*Primary Examiner* — Bruce E. Snow
(74) *Attorney, Agent, or Firm* — Whitham & Cook, P.C.

(57) ABSTRACT

The invention refers to the area of control of a limb device in the form of an artificial limb for a human or a robot limb. In particular, the invention is related to a control unit for electrically controlling an electrically controllable limb device, the limb device comprising a plurality of actuators, the control unit comprising a first interface for connecting the control unit to the limb device, the control unit comprising a second interface for connecting the control unit to a data gathering device comprising one or more sensing devices, the control unit comprising a processing unit which is arranged for controlling the limb device at least based on data gathered by the data gathering device, wherein the control unit is arranged for outputting one single control action step to the actuators of the limb device calculated by the processing unit based on a first data or data combination received from the data gathering device, and the control unit is arranged for outputting a plurality of control action steps to the actuators of the limb device calculated by the processing unit based on a second data or data combination received from the data gathering device, the second data or data combination being different from the first data or data combination, the plurality of control action steps inducing a more complex automatic movement of the limb device that (Continued)

the one single control action step. The invention further refers to a system comprising such a control unit, a method for controlling an electrically controllable limb device and a computer program.

10 Claims, 4 Drawing Sheets

(51) Int. Cl.
  *B25J 9/16* (2006.01)
  *A61F 2/58* (2006.01)
  *A61F 2/72* (2006.01)
  *A61F 2/70* (2006.01)
  *A61F 2/76* (2006.01)

(52) U.S. Cl.
  CPC .............. *B25J 9/161* (2013.01); *B25J 9/1612* (2013.01); *A61F 2002/6827* (2013.01); *A61F 2002/704* (2013.01); *A61F 2002/769* (2013.01); *A61F 2002/7615* (2013.01); *G05B 2219/32014* (2013.01); *G05B 2219/36435* (2013.01); *G05B 2219/39528* (2013.01); *G05B 2219/40139* (2013.01); *G05B 2219/45172* (2013.01)

(56) References Cited

U.S. PATENT DOCUMENTS

| | | | |
|---|---|---|---|
| 2007/0219668 A1 | 9/2007 | Takahashi et al. | |
| 2012/0010749 A1* | 1/2012 | van der Merwe | A61F 2/54 700/264 |

* cited by examiner

CONTROL OF LIMB DEVICE

CROSS-REFERENCE TO RELATED APPLICATIONS

This application is a continuation of U.S. Ser. No. 14/303,229, filed Jun. 12, 2014, now abandoned, claiming priority to European Application 13171671.4 filed Jun. 12, 2013.

BACKGROUND OF THE INVENTION

Field of the Invention

The invention refers to the area of control of a limb device in the form of an artificial limb for a human or a robot limb. In particular, the invention is related to a control unit for electrically controlling an electrically controllable limb device, a system comprising such a control unit, a method for controlling an electrically controllable limb device and a computer program.

While the invention is fully applicable both to the control of artificial limbs for humans and for limbs of robots, in the following description it is mainly referred to the area of artificial limbs for humans, e.g. an arm or hand prosthesis. The limb can be e.g. any extremity, like an arm or a leg.

Background Description

In prior art devices, myoelectric control is used for controlling an electrically controllable limb device. Myoelectric control is the most common method in the literature, and it is in fact the only method that was accepted by the industry and implemented in commercial products. In myoelectric control, muscle activity is assessed by using electromyography (EMG) recordings and the acquired EMG signals are decoded to reflect the intention of the user. The reasons for using myoelectric signals are subconscious control and simple interface. This control method has been in the focus of research already for decades, but it is now evident that there is a large gap between what has been developed and tested in academia, and what has been actually implemented in the working, commercial devices. Basically, only the simplest form of myoelectric control (i.e., two-channel/two-command interface) showed to be robust and practical enough to be applied outside of the research lab. The limitations of this approach are even more evident, as more and more modern, sophisticated prostheses are being designed and launched to the market, e.g., Otto Bock Michelangelo Hand, Touch Bionics i-Limb, RSLSteeper Bebionic Hand. These systems are complex mechanical mechanisms with several independently controllable degrees of freedom. Controlling such a flexible functionality represents a challenging task that is hard to integrate into the classic pattern based, master-slave scenario, in which the user has to control all the aspects of the prosthesis during the execution of a task.

With an amputation, a person suffers also a loss of perception (sensory functions). The current prosthesis can restore the motor functionality to a certain degree, but none of the existing devices offers any kind of soma-somatosensory and proprioceptive feedback, e.g. touch, force, joint positions etc. The idea to close the loop and provide the feedback from the prosthesis to the user has been presented long ago. The lost sensations can be restored using sensory substitution. In this method, the information that was originally received by the lost limb is delivered by stimulating an alternative, still intact sense. For example, the prosthesis can be equipped with the sensors measuring the contact force and joint angles, and the information from these sensors can be delivered by stimulating the skin of the residual limb. The most common methods for the activation of the tactile sense are electrical and direct mechanical stimulation, e.g. by miniature vibratory motors. Although these methods are relatively easy to implement, the resulting feedback channel has limited information transfer due to the inherent limitations of the artificially stimulated tactile sense.

SUMMARY OF THE INVENTION

It is an object of the invention to overcome the aforementioned disadvantages.

The object of the invention is achieved by a control unit for electrically controlling an electrically controllable limb device in the form of an artificial limb for a human or a robot limb, the limb device comprising a plurality of actuators, the control unit comprising a first interface for connecting the control unit to the limb device, the control unit comprising a second interface for connecting the control unit to a data gathering device comprising one or more sensing devices, the control unit comprising a processing unit which is arranged for controlling the limb device at least based on data gathered by the data gathering device, wherein the control unit is arranged for outputting one single control action step to the actua-actuators of the limb device calculated by the processing unit based on a first data or data combination received from the data gathering device, and the control unit is arranged for outputting a plurality of control action steps to the actuators of the limb device calculated by the processing unit based on a second data or data combination received from the data gathering device, the second data or data combination being different from the first data or data combination, the plurality of control action steps inducing a more complex automatic movement of the limb device that the one single control action step.

The invention has the advantage that the control unit which acts as an artificial controller is made more "intelligent" so that it is able to add autonomous decisions to the recognised intentions of the user and therefore automatically do a plurality of control action steps. This requires less involvement of the user. In this way, a conceptual shift compared to prior art concepts is proposed.

The plurality of action steps which are automatically performed by the control unit can be performed simultaneously, which means at the same time, or in a sequential manner. Also, a combination of some simultaneously performed control action steps and some sequentially performed control action steps of the plurality of control action steps can be implemented advantageously.

As explained above, a critical assessment of the current state of the art in the control of active prostheses has shown that the current control methods have serious limitations, especially when the system to be controlled is complex (modern prostheses). For example, advanced, contemporary hand prostheses implement several grasp types such as lateral, palmar, or pinch grip. If the wrist or elbow is also controllable as in, for example, Dynamic Arm from Otto Bock, the arm and hand orientation have to be adjusted as well. The optimal grasp to employ depends on the features of the target object, e.g., palmar grasp for a bottle, and lateral grip for a key. With a conventional myoelectric control, the user operating the prosthesis has to implement several sequential steps each time he/she wants to grasp an object: 1) analyze the object and decide the best grasp type, 2) generate the signals for the selection of a certain grasp type (e.g., several brief muscle contractions), 3) adjust the opening of the hand so that the target object can fit (e.g., several longer muscle contractions), and finally 4) command the hand to close (e.g., one long muscle contraction). If in addition the wrist and elbow joints need to be adjusted, the user has to switch to joint control mode by co-contracting the muscles and then generate the signals to move the joints. Therefore, the user has to go through a sequence of steps, one by one, controlling different aspects of the prosthetic system. Of course, this process can be complicated, long and difficult for the user. He/she has to remember the sequence, generate the proper command signals, change modes (e.g., from grasp selection to hand closing/opening) and remember the available options (e.g., how many grasp types and in which order). This process becomes more complicated for the user as the flexibility of the device increases by the introduction of more grasp types, or more controllable joints. These disadvantages can be overcome by the present invention.

According to an advantageous embodiment of the invention, the control unit is arranged for receiving data via the second interface from the data gathering device which comprises at least 3D (three dimensional) information including depth information, in particular 3D information from surrounding areas of the limb device. With such 3D information including depth information the abilities of the user to control the limb device are further optimized. The 3D information including depth information can be provided by the mentioned stereovision camera arrangement or any other type of sensor which is able to scan the ambient areas and generate such information, like a laser scanner, radar or ultrasonic device.

According to an advantageous embodiment of the invention, the control unit is arranged for receiving data via the second interface from the data gathering device which comprises at least one of camera data, 3D-scanning device data such as stereovision camera arrangement data, laser scanning data, white-light scanning data, and inertial sensing unit data. This has the advantage that additional sensor data for automatically controlling the limb device are available. In prior art devices, the lack of feedback from the prosthesis is a drawback for the users, affecting the performance and acceptance of the system. Since the users do not know the positions of the joints, they have to monitor the prosthesis visually in addition to the object that they are about to grasp, and this is a cognitive burden. Once they have grasped the object, they do not have explicit information about the generated contact force, and this can lead to a breakage or slippage of the manipulated object. These drawbacks are overcome by the present invention. With the additional data it is possible to perform automatically several types of grasp motions, particularly in a more sensitive way than with prior art devices. For example, it is possible to perform some control action steps fully automatically, like selection of grasp type and size, and orientation of the arm and/or hand of the limb device without the need for the user involvement. As a result, the control is simplified and the cognitive burden to the user is minimised. In addition, the control loop is now closed by providing enriched information about the current state of the limb device to the user. In particular, the enriched in-information can contain visual information from the camera and/or the 3D-scanning device. The inertial sensing unit may comprise one or more of accelerometers, gyroscopes and magnetometers.

The 3D-scanning device can be e.g. a stereovision camera arrangement, a laser scanning device, e.g. with pulse shift, time of flight etc., a radar device, a white-light scanning device.

According to an advantageous embodiment of the invention, the control unit comprises a third interface for connecting the control unit to a visual output device to be used by a user of the limb device, wherein the control unit is arranged for outputting visual data to the visual output device based on data received from the data gathering device and/or control steps outputted to the limb device. This has the advantage that information can be transferred to the user by visual means which allows for high information bandwidth in recognising of information by the user.

According to an advantageous embodiment of the invention, the visual device is a stereovision augmented reality device which is arranged for being worn by a user of the limb device, allowing to output visual information to the user which comprises at least 3D information including depth information. This has the advantage that the visual information to be presented to the user can be further enriched by using augmented reality and stereovision. The use of augmented reality has the advantage that the user still has visual contact with the real world, but can be supported automatically by e.g. highlighting certain items on the visual output device with a direct relationship to the real item.

According to an advantageous embodiment of the invention, the control unit is arranged for outputting visual data to the visual output device showing positions of the joints of the limb device. This has the advantage that the user can visually control the operation of the limb device in an improved manner by using additional visual information compared to the usual, unsupported direct view on the limb device.

According to an advantageous embodiment of the invention, the control unit is arranged for outputting a marking signal on the visual output device based upon an internal selection of an object which is to be grasped by the limb device, the marking signal marking the selected object on the visual output device. This has the advantage that the user can use the limb device in a more spontaneous and intuitive way than prior art devices.

According to an advantageous embodiment of the invention, the control unit is arranged for calculating a 3D (three dimensional) orientation of the limb device or a part of it from the data received from the data gathering device and for outputting visual information about the calculated 3D orientation on the visual output device. This has the advantage that the user gets through the visual output device an additional synthetic view on the limb device, wherein the viewing direction can be chosen by the user, without a need for repositioning a camera.

According to an advantageous embodiment of the invention, the control unit comprises another interface for connecting the control unit to a feedback device providing feedback to a user of the limb device, wherein the control unit is arranged for outputting feedback data to the feedback device based on data received from the data gathering device and/or control steps outputted to the limb device. Through the feedback device additional or alternative feedback to the visual feedback can be given to the user. This has the advantage that the feedback given to the user can be further enriched. The feedback device can be at least one of a force feedback device, a tactile feedback device and a temperature feedback device.

According to another object of the invention, there is provided a system comprising a control unit, a data gathering device comprising one or more sensing devices and an electrically controllable limb device in the form of an artificial limb for a human or a robot limb, the limb device comprising a plurality of actuators, the control unit electrically controlling the limb device via the first interface based upon data received via the second interface from the data gathering device. The system comprises the aforementioned advantages over prior art systems.

According to an advantageous embodiment of the invention, the data gathering device comprises at least one of camera, 3D-scanning device such as stereovision camera arrangement, laser scanning, white-light scanning, and inertial sensing unit. This has the advantage that additional sensor data for automatically controlling the limb device are available. In prior art devices, the lack of feedback from the prosthesis is a drawback for the users, affecting the performance and acceptance of the system. Since the users do not know the positions of the joints, they have to monitor the prosthesis visually in addition to the object that they are about to grasp, and this is a cognitive burden. Once they have grasped the object, they do not have explicit information about the generated contact force, and this can lead to a breakage or slippage of the manipulated object. These drawbacks are overcome by the present invention. With the additional data it is possible to perform automatically several types of grasp motions, particularly in a more sensitive way than with prior art devices. For example, it is possible to perform some control action steps fully automatically, like selection of grasp type and size, and orientation of the arm and/or hand of the limb device without the need for the user involvement. As a result, the control is simplified and the cognitive burden to the user is minimised. In addition, the control loop is now closed by providing enriched information about the current state of the limb device to the user. In particular, the enriched information can contain visual information from the camera and/or the 3D-scanning device. The inertial sensing unit may comprise one or more of accelerometers, gyroscopes and magnetometers.

According to an advantageous embodiment of the invention, the data gathering device comprises a 3D data gathering device outputting at least 3D information including depth information.

According to an advantageous embodiment of the invention, at least one of a camera device, an ultrasonic distance sensor, a laser pointer and a laser scanner is mounted on the limb device. This has the advantage that the control of the limb device can be improved through additional sensing and pointing devices. For example, by means of the camera device mounted on the limb device an additional view on objects to be grasped can be given to the user. By an ultrasonic distance sensor the approaching process of the limb device to an object to be grasped can be controlled more efficiently and be made smoother. The laser pointer can be used to point to items to be grasped by the limb device in order to highlight them in the real world. Further, a laser scanner can be used for optimising movement of the limb device to an item to be grasped.

According to an advantageous embodiment of the invention, the system comprises a visual output device which is connected to the control unit through its third interface. This has the advantage that the user can be supported with visual information through the visual output device.

According to an advantageous embodiment of the invention, the visual output device comprises at least one a display or a stereodisplay, a camera or a stereovision camera arrangement. This has the advantage that the system, in particular the control unit, can control whether internally calculated visual information (virtual information) or information from the real world (real information) or a mixture thereof is visualised through the visual output device. In such case the real information is captured by the camera or stereovision camera arrangement.

According to an advantageous embodiment of the invention, the system comprises a feedback device which is connected to the control unit through another interface of the control unit, the feedback device providing feedback to a user of the limb device controlled by the control unit based on data received from the data gathering device and/or control steps outputted to the limb device. The feedback device can be at least one of a proprioceptive feedback device and a system feedback device. In case of a proprioceptive feedback device, feedback can be given in terms of relative limb position, grip type, temperature, surface condition, material condition like soft, slippery, rigid etc. In case of a system feedback device, feedback can be given in terms of system status, status of energy source etc. The feedback device can be at least one of a force feedback device, a tactile feedback device and a temperature feedback device.

According to a further object of the invention, there is provided a method for controlling an electrically controllable limb device by a control unit, the limb device being in the form of an artificial limb for a human or a robot limb, the limb device comprising a plurality of actuators, the control unit comprising a first interface for connecting the control unit to the limb device, the control unit comprising a second interface for connecting the control unit to a data gathering device comprising one or more sensing devices, the control unit comprising a processing unit which is arranged for controlling the limb device at least based on data gathered by the data gathering device, wherein the control unit outputs one single control action step to the actuators of the limb device calculated by the processing unit based on a first data or data combination received from the data gathering device, and the control unit outputs a plurality of control action steps to the actuators of the limb device calculated by the processing unit based on a second data or data combination received from the data gathering device, the second data or data combination being different from the first data or data combination, the plurality of control action steps inducing a more complex automatic movement of the limb device that the one single control action step.

According to an advantageous embodiment of the invention myoelectric control is used only for triggering, supervising and fine tuning of the automatic operations of the control unit. In this way, myoelectric information is still used for control of the limb device, but more in a background fashion, in order to release the user from too much burden in activating several detailed movements of the limb device through its muscles.

According to a further object of the invention, there is provided a computer program which is arranged for executing any of the aforementioned methods if the computer program is executed on a processor of the control unit controlling the limb device. The computer program can be stored on a storage medium, like a hard disk, a CD or any kind of semiconductor memories, like a memory stick.

In summary, the present invention comprises, among others, the following aspects and further advantages:

A major improvement within the control is the use of the artificial vision in both closed loop automatic control of the prosthesis and the augmented reality feedback to the user. The new control will allow the prosthesis to accomplish several tasks autonomously; therefore, decrease the burden on the user and greatly improve the performance. Importantly, the user would still preserve her/his supervisory role by triggering, monitoring and correcting the performance.

The augmented reality feedback exploits the high bandwidth and fidelity of the artificial visual and human perception system, and overcomes the limitations of the tactile feedback. The proposed scheme is not excluding tactile and proprioceptive feedback coming from the sensors integrated in the hand; yet, the artificial vision conveys unique information during a prehension and preparation phases that cannot be provided using the "built-in" position and force sensors.

A major improvement of the invention is that the reach/grasp functions can be based on the integration of vision, perception, skills, and fine tuning based on the tactile/force feedback.

We propose a novel control method in which some control steps are implemented fully automatically, e.g., selection of grasp type and size, and orientation of the arm/hand, without the need for the user involvement. As a result, the control is simplified, and the cognitive burden to the user is therefore minimized. In addition, we close the control loop by providing rich visual information about the current state of the prosthesis to the user.

In this invention, we propose a system for the closed loop control of grasping and orientation in the arm/hand prosthesis. The control of grasping includes the possibility of automatic selection of the grasp type and aperture size that are appropriate to grasp the target object. The control of reaching refers to automatic adjustment of the hand joint angles so that the hand is properly oriented to implement the most appropriate grasp.

We also propose to close the control loop by providing to the user a visual feedback about the state of the prosthesis (e.g., joint angles, grasping force). Using augmented reality, we can convey rich, high fidelity information with an information bandwidth that is significantly higher compared to a conventional, tactile feedback.

A major improvement of the proposed invention is to enrich the artificial controller by providing it with some extra sources of information in addition to the classically used muscle electrical activity. In this way, the artificial controller becomes capable of making autonomous decisions and operating the hand automatically and with minimal involvement of the user. The controller analyses the properties of the target object and automatically selects the grasp type and size, and adjusts the orientation of the hand to appropriately grasp the object.

The system employs stereovision implemented using special augmented reality glasses with two cameras to obtain a 3D structure (geometrical model) of the scene and the target object. Since the controller has the information about the geometry of the target object, it can autonomously determine the most appropriate way to grasp the object. Therefore, the controller automatically selects the grasp type and the size of the hand opening. Next, an inertial sensor is mounted onto the artificial hand providing information about the hand orientation. This can be compared to the orientation of the object, which is derived from the stereovision processing, and used to 1) readjust the hand based on the direction (object side) the hand approaches the object, and/or 2) to control the hand orientation by adjusting the wrist (and elbow) joints of the prosthesis. Finally, the augmented reality glasses are used to provide to the user a rich visual feedback about the current state of the prosthesis. This feedback is projected into the scene as a virtual object seamlessly integrating with the real environment. The feedback provides information about the position and orientation of the prosthesis, and also about the grasping force generated by the hand. This information can be used by the user to supervise the operation of the artificial controller, and when needed, to fine tune or correct the eventual mistakes made by the automatic control system. A simple myoelectric control interface is used to trigger the automatic controller and, when needed, to manually control the prosthesis in a closed loop by using the feedback.

According to an exemplary practical application, the user wears augmented reality glasses, inertial sensor(s) is placed on the prosthesis and myoelectric control interface is in place. The user looks at the target object and triggers the hand opening by using a simple myoelectric command, e.g., finger extension. The hand automatically preshapes, i.e., the grasp type and size are automatically selected by analyzing the geometrical properties of the target object. A virtual object representing the prosthesis aperture and orientation is projected into the real scene just next to the object to be grasped. By comparing the properties of the virtual object with the target object, the user can fine tune or correct the grasp using myoelectric control. Using the information from the inertial sensor, the controller reacts and automatically readjusts the grasp depending on how the user approaches the object (e.g., from which side). If more proximal joints are available (wrist and elbow), the controller adjusts the orientation of the prosthesis during reaching in order to properly position the hand for the grasp. When the hand is positioned around the object, the user gives a command for the hand to close. A virtual object representing the contact force is projected into the real scene just next to the object to be grasped. The user controls the grasping force using myoelectic control and augmented reality force feedback information.

As mentioned, the overall control paradigm is novel. Conventional control methods rely on the user to make all the decisions and send control signals to implement those decisions. In our approach, the controller is more "powerful" and brings autonomous operation to the artificial hand. The user merely triggers, supervises and corrects the system. This decreases the cognitive burden from the user.

The application of stereovision for the automatic control of the limb device, e.g. of grasping and reaching with the hand/arm prosthesis, is novel. To coordinate the two separate control systems, we employ a simple myoelectric interface (two channels) to decode the user intentions and inertial sensors to assess how he/she moves the prosthesis.

The use of augmented reality (AR) to provide the rich visual feedback about the current state of the limb device is novel. AR was not applied before in the context of the closed loop control of limb devices, e.g. hand/arm prosthesis. The latter represents a fully wearable and mobile application of AR.

The AR feedback is used not only to provide the status of the prosthesis variables, but also to establish the communication between the artificial controller and the user. For example, the system indicates to the user the object that is currently selected by the system as the target for grasping by marking it using a flickering red patch.

The application of inertial measurement units to measure the prosthesis orientation is novel, and the integration of inertial and stereovision data for the control of hand/arm configuration/orientation.

The proposed combination and integration of different technologies (stereovision, augmented reality, inertial units and myoelectric control) into a complete solution for the closed loop control of the limb device is a novel and unique approach in this field.

The control of grasping and reaching (orientation) for electrically powered hand/arm prosthesis is a complex task. Myoelectric control is intuitive and simple to implement, but it is effective only when applied to the simplest systems, e.g. single degree of freedom. If there are more degrees of freedom available, they have to be controlled sequentially, one by one. For example, if the prosthesis implements several grasp types, the user first has to generate muscle activity to select the active grasp and then he/she generates muscle activity to control the hand opening/closing. If there is an active wrist, the user has to change the control mode from hand opening/closing to wrist joint control in order to adjust the orientation. In order to accomplish this, the user needs to know the system and the control interface very well, which means that he/she has to go through a tedious and long training process. In addition, since the user has to go through a sequence of steps, controlling every single detail in this sequence, the whole process can represent a significant cognitive burden.

In this invention, we propose a system that implements the control of grasping and hand orientation in a fully automatic way (transparently to the user). The user has to look at the target object, which is done anyway, and trigger the system, and the artificial controller analyses the object properties and autonomously decides and controls the grasp type, size and hand/arm orientation. Since this is done fully automatically, the cognitive burden is truly minimized.

In this invention, we propose the use of augmented reality (AR) provided through an AR glasses to implement a rich visual feedback to the user. Vision has significantly higher bandwidth compared to the tactile sense. The visual feedback can convey rich, high fidelity information in a way which is easy to understand. At the same time, the user needs a minimal training to utilize the feedback successfully. This is contrary to conventional feedback interfaces that are limited to relatively simple information and where a significant training is needed for the user to learn how to decode the information communicated by the system. Since we rely on AR, the feedback is naturally embedded into the real scene. It is therefore nonintrusive, and it can be positioned in a way that minimizes the interference with the rest of the scene. For example, in our current prototype, a virtual feedback object is placed next to the target object to which the user is looking, minimally blocking the other aspects of the scene.

As pointed out in the following description, our system and method is highly modular. The components stereovision control, augmented reality feedback, inertial sensing are self-contained units that can be employed in combinations, using sensor fusion, or individually. This loose coupling between the modules decreases the level of risk: a single part, a subset of components, or the system as a whole can grow into a successful product.

BRIEF DESCRIPTION OF THE DRAWINGS

The invention is now described by some examples using drawings.

The drawings show in

FIG. 3—the overall design of the system, and.

DETAILED DESCRIPTION THE INVENTION

Figure 1:
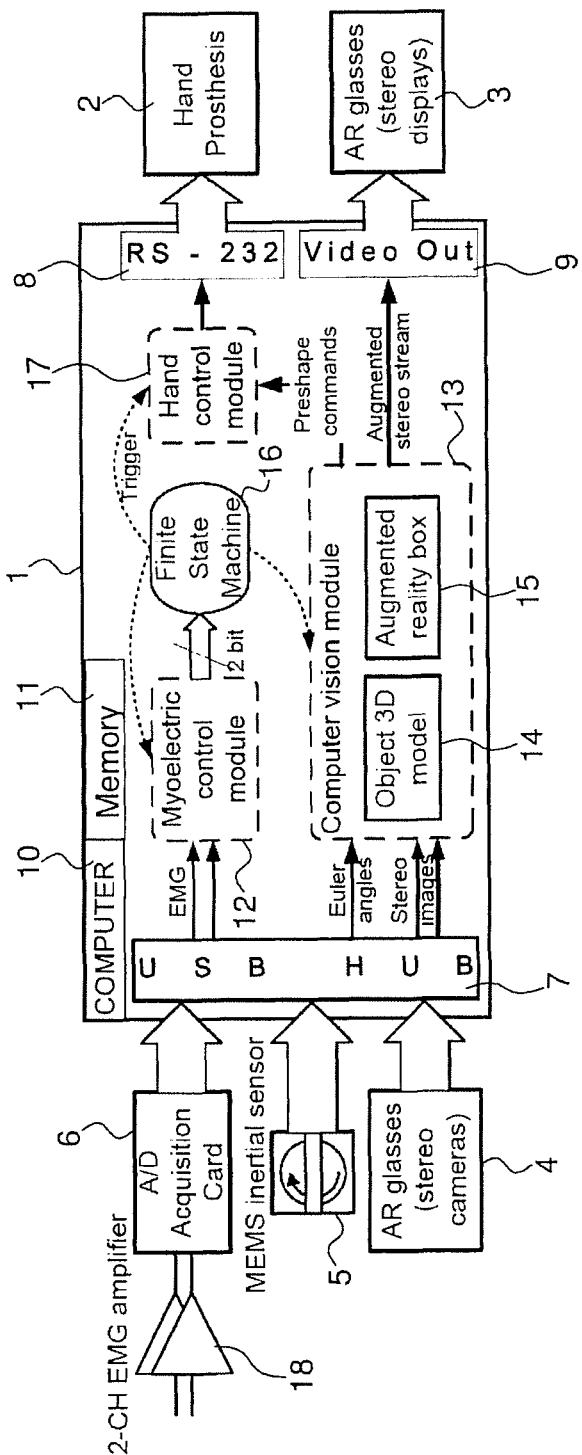
FIG. 1—an overview of a system of the invention.

The invention that we have developed implements both feedforward and feedback pathways providing the user with the possibility to control the prosthesis in a closed loop. We use computer vision in stereo configuration to emulate the aforementioned process of grasp planning in an able bodied human. The computer vision methods are employed to analyze the scene, segment out the target object, analyze its 3D properties and automatically select the grasp type and size appropriate for the object. To implement stereovision, we use special augmented reality (AR) glasses that are equipped with a stereo camera pair. At the same time, we use the glasses to provide an advanced visual feedback (in the form of AR) about the current state of the prosthesis. Since AR objects are integrated into the real scene, this feedback is simple, intuitive and effective, and at the same time, it can convey rich and high fidelity information, since the visual sense has a large bandwidth. Finally, we use inertial sensors to assess the current orientation of the hand and we fuse this information with a 3D model of the target scene (available from the stereo vision engine).

The resulting system implements a high level automatic control of grasping and provides a rich feedback to the user by fusing several information sources. In this scenario, the myoelectric control is reduced to triggering, supervising and fine tuning of the automatic operations of the system. As a result, a significant part of the burden from the user is relocated to the artificial control system. Importantly, this approach is powerful enough to control systems of almost arbitrary complexity, e.g. from an artificial hand to a full arm. The proposed system and method is an example for the use of sensor fusion in the control of prosthesis, which is the approach recommended as the way to go in the future developments within this field.

We demonstrate a system of the invention by using a transradial prosthesis, i.e. artificial hand, as the example limb device to be controlled. The hardware includes the following components (see FIG. 1): transradial prosthesis 2, augmented reality glasses 3, 4, EMG input channels 6, 18, inertial measurement unit (IMU) 5, control unit 1, which can be e.g. a standard laptop. In the sequel, we described the components individually.

Transradial Prosthesis 2

We use one of the modern, flexible prosthesis, e.g. SmarthHand from the Biorobotics lab of Scuola Superiore Sant'Anna, Italy. The system has independently controllable fingers, and this can be exploited to implement several grasp types (palmar, pinch, lateral and spherical) and to control the aperture size. The prosthesis is equipped with position and force sensors; therefore, we can read the current finger positions and contact force. This information is used to provide the feedback to the user.

EMG Input Channels 6, 18

The EMG input channels 6, 18 comprise of two channels of bipolar EMG. Each channel has an amplifier 18. The signals of the amplifiers 18 are fed to an analogue to digital converter, e.g. an A/D acquisition card mounted in the standard laptop. The channels will be placed on the residual limb over the muscles that flex and extend the fingers, i.e. open/close the hand. This component is used to implement a simple two channel myoelectric control that is used to trigger and fine tune the automatic operation of the system.

Augmented Reality (AR) Glasses 3, 4

We use the model Vuzix iWear920AR. The model has two cameras in the form of a stereovision camera arrangement 4 that are built into the right and left "glass". Just behind the cameras, there is a visual output device 3 in the form of two video panels projecting the video streams from the cameras. The video panels implement a stereoscopic 3D video, meaning that the wearer (user) looking into the panels receives a 3D picture of the scene in front of him. The video streams captured by the two cameras are inputs for a stereo vision algorithm in the control unit 1, which is used to build the 3D model of the scene, analyze the target object and decide grasp type and size. Before projecting the captured streams back to the panels, the video can be processed, and virtual objects can be integrated into the scene. This method is used to provide the AR feedback to the user.

Inertial Measurement Unit 5

This is a cluster of sensors, including accelerometers, gyroscopes and magnetometers (XSens M420). The information from these sources is combined, and the unit estimates a 3D orientation of the object to which it is attached. This is used to provide the feedback about the current orientation of hand, and also to control the hand during reaching.

Control Unit 1

Any computer, e.g. a standard laptop, can be used to implement the signal processing and control algorithms. The control unit 1 receives the inputs from the other components, processes the data and sends the control commands.

For example, the control unit 1 can also be implemented as en embedded system, e.g. by using a microprocessor or microcomputer for the signal processing and control algorithms. The components can be miniaturized and integrated into the hand prosthesis 2 itself. For example, myoelectric hands already have built-in EMG amplifier and electrodes. Also, a specialized processing unit (embedded, small factor system) with a powerful DSP processor can be used. FIG. 1 is a schematic representation of the system with its processing modules and data flow.

In the exemplary embodiment the user operates a transradial prosthesis 2. The EMG amplifier 18 provides two channels of bipolar EMG taken from the finger flexor and extensor muscle groups. This is a simple myoelectric control interface for the triggering of the automatic control. The user wears augmented reality (AR) glasses 3, 4 providing the video streams from the stereo camera pair 4, which is the input for the computer vision algorithm, and visual feedback to the user in the form of virtual objects embedded into the real scene. The inertial measurement unit 5 is placed onto the artificial hand 2 to measure its 3D orientation.

The control unit 1 comprises of a computer, e. g. in the form of a microprocessor or microcontroller 10 and a memory 11 where a control program in the form of a computer program is stored. The control unit further comprises several interfaces 7, 8, 9 which connect the control unit 1 to the external elements. A first interface 1, e. g. in the form of a serial data interface, e. g. a RS-232 interface, connects the control unit 1 to the hand prosthesis 2 or any other limb device. A second interface 7, e. g. in the form of an USB hub, connects the control unit 1 with any of the data input sources 4, 5, 6 which together form the data gathering device. A third interface 9, e. g. in the form of a video out interface, connects the control unit 1 to the stereo displays 3 of the AR glasses, or to any other video output device.

The control unit runs several control processes, e. g. in the form of software processes executed by the computer 10. A first process 12 is a myoelectric control module which receives the digital EMG signals and outputs signals derived from the input signals to a control block 16 which is a finite state machine. Upon the signals of the myoelectric control module 12 the finite state machine outputs trigger signals which are marked in FIG. 1 by the dotted arrows. E. g. the finite state machine 16 could trigger another control module which is a hand control module 17. The hand control module 17 outputs control action steps through the first interface 8 to the actuators of the hand prosthesis 2.

Another control module is a computer vision module 13 which comprises an object 3D model 14 and an augmented reality box 15. The computer vision module 13 can be triggered by the finite state machine 16. The computer vision module 13 receives signals from the elements 4, 5, 6 of the data gathering device through the second interface, e. g. it receives Euler angles and stereo images. The computer vision module 13 outputs preshape commands to the hand control module 17. Further, the computer vision module 13 outputs an augmented stereo/video stream through the third interface 9 to the stereo displays 3.

Processing modules and data flow: The computer 10 implements signal acquisition and processing. The myoelectric control module 12 processes the recorded EMG and detects the activity of the finger flexor and extensor muscles. The binary information about the muscle activity drives the state transitions within the finite state machine 16 implementing the overall control logic (explained in the text). Computer vision module 13 receives the stereo images and reconstructs the 3D geometrical model of the scene and of the object that is the target for grasping. Based on this and the information about the hand orientation (inertial measurement unit 5), the hand control module 17 decides the grasp type and aperture size appropriate to grasp the object. Hand control module 17 sends the commands to the hand prosthesis 2 to implement the desired grasp strategy. Computer vision module also receives the sensor data from the hand prosthesis (position and force) and uses this to augment the video stream before it is re-projected to the glasses to provide the visual feedback to the prosthesis user. The processing is organized in a sequential manner and the modules are activated (triggered) by the finite state machine.

Figure 2:
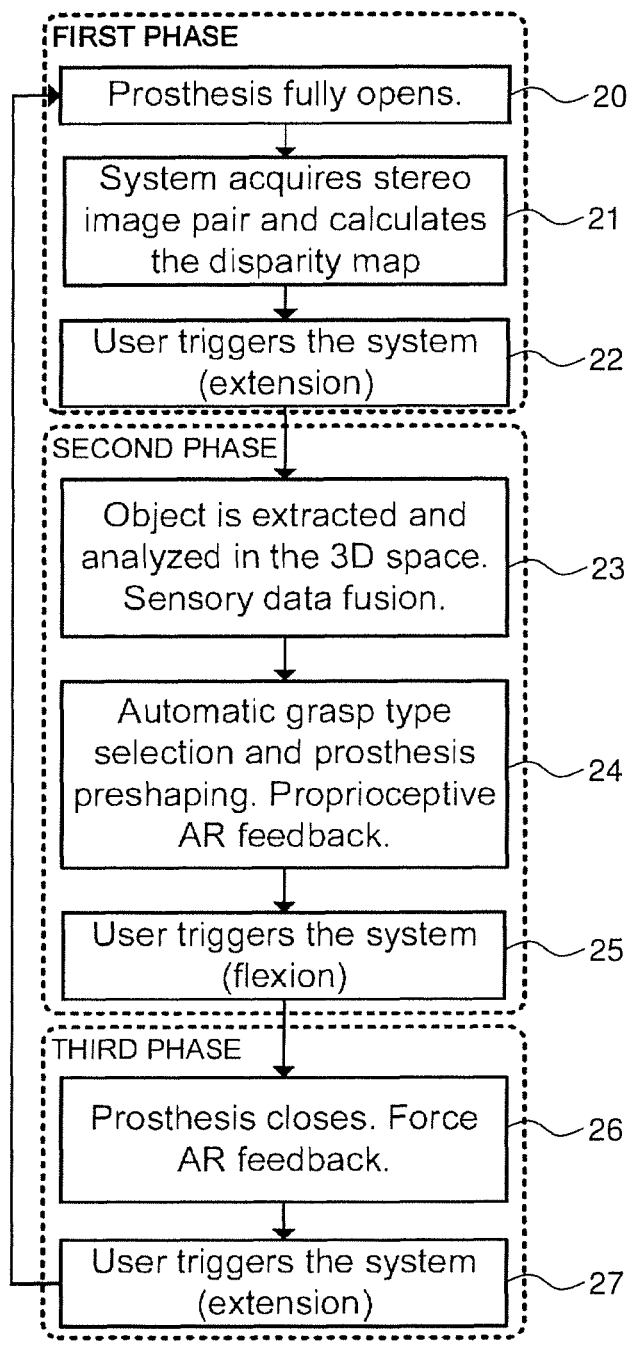
FIG. 2—a diagram showing a first aspect of the system operation.

FIG. 2 shows the system operation. There are e.g. eight steps 20, 21, 22, 23, 24, 25, 26, 27 comprising the control loop of the system.

As can be seen in FIG. 2, the control loop is segmented in three phases, a first phase, a second phase and a third phase. In the first phase, which comprises steps 20, 21, 22, in step 20 the prosthesis is commanded to fully open. Then in step 21 the system acquires a stereo image pair and calculates the disparity map. Then, in step 22 it is expected that the user triggers the system by an extension of a finger.

The second phase comprises of steps 23, 24, 25. In step 23, an object is extracted and analysed in the 3D space. Then a step of sensory data fusion is executed. Then in step 24 an automatic grasp type selection and prosthesis preshaping is executed. Proprioceptive AR feedback is given. Then in step 25 it is expected that the user triggers the system, e. g. by a flexion movement.

Finally, the third phase comprises of steps 26 and 27. In step 26 the prosthesis closes. The existing force is signalled by AR feedback. Then in step 27 it is expected that the user triggers the system, e. g. by an extension of a finger.

In more detail, a target object selection can be performed by:

a) the user focuses on the target object,
b) the computer vision module estimates the depth map and segments the objects,
c) the object closest to the center is selected as the target, and the user sees the object marked by a flickering red color on the stereo displays 3; the user issues the command for hand opening, and this starts the hand preshaping phase,
d) a geometrical model of the object is constructed, e) a set of rules is used to select grasp type and size based on the estimated object properties, and the hand is commanded to preshape, f) a virtual object is embedded into the real scene (augmented reality) providing the information about the hand aperture size and orientation; the user places the hand close to the object and generates command for closing, g) the hand closes around the object and h) a virtual bar is embedded into the real scene depicting the current grasping force (bar length and color).

The control loop operates sequentially, following the steps below:

1) Target Object Selection

The user observes the scene and "locks on" the object that he would like to grasp. This is performed by orienting the head and thereby the AR glasses 3, 4 so that the desired object comes close to the center of the field of view. The computer vision module continuously analyzes in soft real time the stereo video stream, estimates the 3D structure of the scene, establishing a depth map, and segments the objects. The object that is located most centrally is chosen by the system to be the target for grasping. To facilitate this process and make it transparent for the user, the system "communicates" with the user using augmented reality: the object that is currently chosen by the system is marked by a flickering red color.

2) Hand Opening

When the user selects the object, she/he gives the command for the hand to open by activating finger extensors. Note that this corresponds to the muscle activity in able bodied subjects, i.e. finger extensors/flexors are normally activated when opening/closing the hand.

3) Hand Preshaping

Computer vision module provides the 3D properties of the target object (position, orientation, and geometrical model. The objects are modeled as cylinders, boxes, spheres and lines, in case of thin and long objects. This set of geometrical primitives covers the general shape of the most of the common daily life objects. The object features are input for a set of simple rules designed to emulate the cognitive process during grasp selection in able bodied individuals. The rules have IF-THEN structure: for example, if the object is cylindrical and wide, the palmar grasp is used, if the object is a thin box, lateral grasp is employed etc. After the grasp type is selected, the aperture size is determined. The hand should open so that the aperture is wider than the object, but not too wide as this can compromise the formation of a stable grasp, e.g., the fingers could push out the object while trying to close around. The appropriate aperture is calculated by adding a safety margin to the estimated object width. The hand is commanded to preshape according to the selected grasp strategy.

4) AR Feedback (Proprioception) with Manual/Automatic Adjustment of Aperture

The proprioceptive AR feedback is shown revealing to the user the current hand aperture and orientation. The virtual box is embedded into the real scene next to the target object and along the side from which the object is supposed to be grasped by the user. The size of the virtual box is continuously updated to represent the current hand aperture size, i.e., the box stretches and shrinks, while the orientation of the box follows the orientation of the hand, i.e., the box rotates. Since the virtual box is placed next to the object, the user can easily compare the current state of the hand with the actual properties of the target object, evaluating the conditions for the stable grasp. Importantly, this can be done without focusing to the hand and even while the hand is out of the user's field of view.

In the case when the hand aperture is not appropriate, e.g. wrong estimation from the computer vision module, it can be adjusted by using simple myoelectric control, i.e. to open/close the hand more, the user activates finger extensor/flexor muscles. Therefore, by exploiting the AR feedback, the user can correct and/or fine tune the automatic decisions of the artificial control system. At the same time, the system can recognize and react to the current activates of the user. For example, since the system "knows" the current orientation of the hand, it can detect that the user decided to approach the object from a different side with respect to the one suggested originally by the system. Therefore, the hand can be reshaped. The grasp size and even type can be changed reactively.

5) Hand Closing

When the user estimates that the hand configuration is appropriate, she/he issues the command for closing. This is done by activating finger flexor muscles, which again corresponds to the way these muscles are used in able bodied subjects.

6) AR Feedback (Force) with Manual Force Control

Once the contact with the object is detected, AR feedback of grasping force is started. The bar indicating the current force appears next to the object, e.g. a red bar. The bar length and color are proportional to the force amplitude. This is direct and intuitive information about the variable (force) that is almost completely unobservable under the usual conditions, i.e., a conventional prosthesis without feedback.

The system of the invention is modular and flexible. Most of the components can be used as standalone functional modules. For example, the control based on stereo vision or the feedback via augmented reality could be used on their own, without the integration with each other or the other components.

Many aspects of the aforementioned control loop can be easily extended to accommodate more sophisticated features. During the target object selection, eye tracking can be used to determine the object that the user is currently looking at. Importantly, the eye tracking algorithm might be embedded into the glasses. For the hand preshaping, a general high fidelity model (triangle mesh) of the target object can be used instead of the limited set of predefined geometrical primitives. The AR proprioceptive feedback can be implemented by using more sophisticated graphical representation, e.g., graphical model of the hand. The same is true for the force feedback. During the approach phase, if the hand has a wrist rotator, the orientation of the hand can be automatically readjusted so that the hand grasps the object from the side (and/or at the sites) that was selected previously during the grasp planning. If prosthesis is more complex, e.g. whole arm, the stereovision algorithm can drive all the degrees of freedom during reaching and grasping.

An important step in stereo processing is the depth (disparity) estimation, which is the method to estimate a distance from the cameras for some or all of the pixels in the image. The success of this step has a major impact on the quality of all further image-processing phases. An efficient Large-scale Stereo Matching (ELAS) algorithm is applied to a grayscale image pairs to determine the depth map. The 3D coordinates for each pixel are then easily obtained by combining pixel disparity information and intrinsic camera properties (triangulation).

The scene analysis is started by identifying the surface on which the objects are placed, i.e., a surface of the table. This base surface is modelled geometrically as a simple plane. The target object located on the base plane is modelled as a box, cylinder, line or sphere. These geomet-geometrical primitives are determined by assuming a certain model and fitting it through the point cloud (pixels with 3D coordinates) using RANSAC algorithm; the model with the best fit is adopted to represent the shape of the object. This process is described below:

Plane: three support points in the point cloud are determined that have the largest number of inliers (where an inlier is every point that has a distance to the plane of less than 0.3 cm).

Box: The method iteratively fits planar surfaces until it finds two planes with compatible orientation (i.e., they must intersect and form an angle that is close to 90°). Using the intersection line, directions of these two planes and of the remaining faces are reconstructed and a semi closed 3D patch structure is formed.

Cylinder: The method searches for a set of three points that form a circle in the 3D space, which when extended to cylinder contains the largest number of inliers (distance from surface less than 0.2 cm).

Line: A line is fitted through set of points using LSQ method and the most common length of all other lines that are perpendicular to it is determined.

To provide the AR feedback, a virtual box object is embedded into the real scene. This is done by forming a 3D model of the AR box within the existing point cloud, and then finding its visible faces from the users' perspective and back projecting them on the left and right 2D camera image planes. The end result is an augmented reality box object that appears as a part of the real scene observed by the user.

Figure 3:
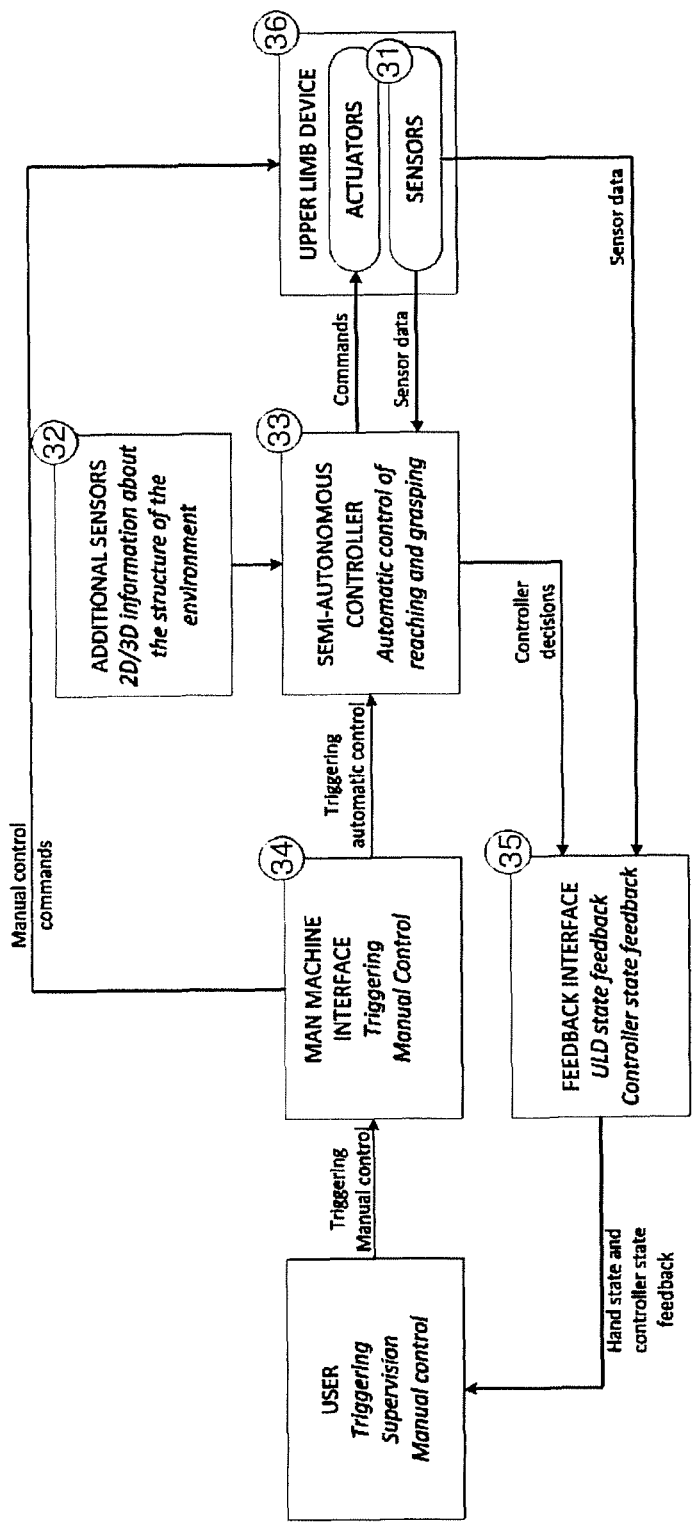
Figure 4:
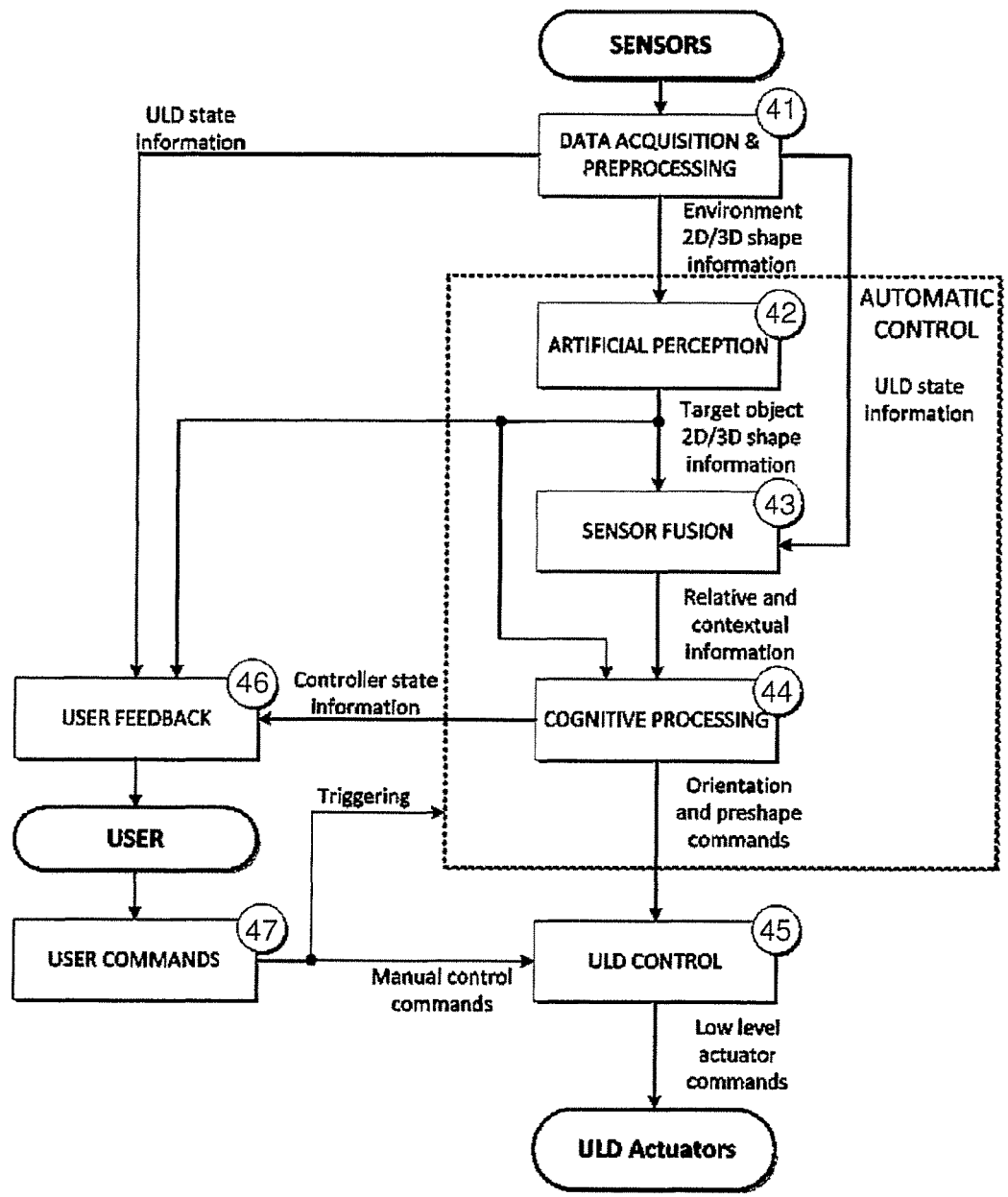
FIG. 4—a diagram showing a second aspect of the system operation.

In the following, the invention is further explained using FIGS. 3 and 4.

Generally, the invention presents a method and a system for the semi-autonomous closed loop control of a multi degree of freedom (DOF) upper limb device (ULD) for the assistance of reaching and grasping. In particular, the upper limb device can be a prosthesis (e.g., artificial robotic hand or arm) or an orthosis (e.g., robotic exoskeleton). In summary, the system integrates:

1) An artificial controller that combines the state of the art technologies (e.g., computer vision, inertial sensors, augmented reality, and myoelectrical control) in order to perform a fully autonomous operation of the ULD during typical reaching, grasping and manipulation tasks (e.g., automatic preshaping of the gripper, control of reaching and orientation of the ULD/gripper).
2) Artificial feedback interface providing to the user the missing proprioceptive and grasping force sensory information from the ULD, thereby implementing the user-driven closed loop control of the ULD.
3) Bilateral communication interface to support the shared control between the user and the semi-autonomous controller. The user supervises the automatic operation of the system using feedback interface (controller=>user), and in any moment in time, he/she can correct, fine tune or override the autonomous operation using manual control (user=>controller).

The invention comprises a modular system and a method for the semi-autonomous closed loop control of a multi-DOF upper limb device (ULD) for the assistance of reaching and grasping. The system comprises at least fol-following components (see FIG. 3):

31: A set of sensors providing information about the current state of the ULD and its interaction with the environment.

32: A set of sensors providing high fidelity information about the 2D/3D spatial structure of the environment, from which the properties of the object that is the target for reaching/grasping (hereafter target object) can be estimated. This can be e.g. the stereo cameras 4 of the AR glasses.

33: A semi-autonomous programmable electronic controller (hereafter controller) that fuses the data from the sensors 31 and 32 and based on this automatically (without user intervention) controls grasping and/or reaching functions of the ULD. The controller 33 can be the control unit 1.

34: Man-machine interface to capture and decode the commands from the user. The commands are received by the controller 33 and used to trigger, supervise, correct, fine tune and/or override the automatic operation of the system.

35: Feedback interface providing to the user online information about the state of the ULD and/or controller.

36: An upper limb device, i.e., the system to be controlled.

In one particular implementation, the ULD is an electrically controlled upper limb prosthesis or an upper limb robotic exoskeleton. ULD is a multi DOF mechanical system comprising an arbitrary number of actuators that can be individually controlled and sensors measuring the device state and/or interaction with the environment.

In one particular implementation, the sensors 31 are embedded into the ULD and measure the position of the ULD articulations (e.g., join angles), interaction forces (e.g., grasping force), orientations of the ULD segments (e.g., inertial measurement units) or any other internal/interaction variable of interest (e.g., temperature, vibration). Alternatively, the sensors can be placed externally onto the ULD or they can be integrated into the controller 33 (see below). The externally placed sensors can be connected to the controller using any wired or wireless communication link.

In one particular implementation, the sensors 32 include any sensing device that can provide the information about the structure of the environment from which the properties of the target object can be estimated. This could be ultra sound sensors, laser scanners or active imaging devices such as a time of flight camera and structured light sensors (e.g., Kinect) and/or passive imagining devices such as single or multiple video camera systems (e.g., stereo camera pair). These sensors provide 2D/3D image of the scene and the target object. The sensors can be embedded into the ULD, mounted externally onto the ULD or they can be worn by the user. Possibly, the sensors can be integrated into the feedback interface 35 (see below). For example, a camera can be integrated into the hand prosthesis or embedded within the frame of the augmented reality (AR) glasses. The communication link between the controller and the sensors can be wired or wireless.

In one particular implementation, the controller 33 can be an embedded real time system integrated into the ULD or an external programmable electronic device. The latter can be a custom made unit or a general purpose processing element such as a smartphone. In both cases, the controller can have integrated sensors (e.g., a smartphone with an accelerometer or a camera) that can be used within the system as the sensors 31 or 32.

In one particular implementation, the controller 33 uses 2D/3D information about the target object provided by the sensors 32 to automatically preshape the gripper of the ULD so that its configuration is convenient for grasping the target object. For example, the controller estimates the properties (shape and size) of the target object from a 2D/3D image of the scene provided by an imaging device. Based on this, the controller selects a grasp type from a predefined set of implemented grasps and adjusts the size of the hand opening so that the object fits nicely into the hand. Also, the controller could directly adjust individual finger joints taking into account detailed information about the object shape.

In another particular implementation, the controller 33 combines 2D/3D information about the target object obtained from the sensors 32 and the information about the state of the ULD from the sensors 31 to automatically control the reaching movement towards the object as well as the orientation of the gripper. For example, the controller estimates the orientation of the target object from the acquired 3D image. From the position and orientation sensors within the ULD, the controller determines the current orientation of the ULD. Based on this, it calculates the reference reaching trajectory and transports the ULD from its current position to the vicinity of the target object. At the same time, the controller adjusts the joints of the ULD so that at the end of the reaching movement the gripper is positioned conveniently to grasp the target object. The control of reaching and orientation accommodates the active joints of the ULD. For example, in the case of a robotic prosthetic hand the wrist joint is controlled (e.g., orientation of the gripper), while the shoulder, elbow and wrist are controlled in the case of a full arm prosthesis (e.g., both reaching and gripper orientation).

In yet another implementation, the controller 33 uses the information from sensors 31 and 32 to make the ULD dynamically respond to user actions and intentions. For example, by monitoring the ULD orientations (through sensors 31) and by knowing the orientation and shape of the target object, the controller can detect the side the user is approaching the target (e.g., short or long side) and reconfigure the gripper accordingly (e.g., smaller or larger opening).

In one particular implementation, the controller 33 selects the target object from a set of detected objects as the one that is the closest to the center of the 2D/3D image provided by the imaging device. In another particular implementation, a miniature eye tracking device is integrated into the system. The controller then selects the target object as the object to which the user points his/her gaze.

In one particular implementation, the man machine interface 34 is implemented using myoelectric control and/or other sensors. It acquires the command signals from the user and converts them into system actions. The user manual commands have the highest priority and always override the decisions of the controller. Put differently, the user can take over the command of the system in any moment, and manual control has precedence over the automatic control. In principle, any of the currently available technologies for implementing the communication between man and machine can be exploited to implement this component (e.g., voice, brain machine interface). In one possible implementation, inertial measurement units can be used to detect the movement and determine the user intensions in parallel to the conventionally used myoelectric control, making the overall man-machine interface more robust.

In one particular implementation, the feedback interface 35 can be a wearable visual display. For example, in the most basic version, this can be a display attached to the prosthesis. Alternatively, for the more sophisticated implementation and better performance, this can be a semitransparent or nontransparent augmented reality (AR) glasses or contact lenses designed either for monocular or stereoscopic viewing. These devices can also integrate a variety of additional sensors (e.g., inertial sensors, global positioning sensors, cameras), and these can be also used as the sensors 32 providing multimodal information about the environment. AR is used to transmit the visual feedback to the user about the current state of the ULD or the controller. A virtual object embedded into the real scene can convey, for example, the configuration of the ULD (artificial proprioception) or interaction forces (artificial force feedback) or the selected grasp type and the planned final orientation of the ULD (controller state feedback). The visual feedback virtually places the ULD within the field of view of the user, even when the physical device is outside of his/her field of view. Therefore, it emulates the biological condition and makes the control more efficient, since the sensor data about the device state are always available (ULD state feedback). Also, the user has an insight into the operation of the automatic control (controller state feedback), which he/she can use to supervise the autonomous operation and revert to manual control whenever needed. Furthermore, the feedback can be used to provide the information that is normally not directly observable (e.g., force, temperature) or more precise/detailed information about the device state (e.g., amplified small finger movements during a fine manipulation task). Virtual object(s) conveying the feedback can have different forms, from simple to very sophisticated. For example, a virtual bar plot placed in the peripheral visual field of the user can represent the current opening or grasping force of the ULD gripper. Or, the grasp type automatically selected by the controller can be represented to the user even before the gripper assumes the selected shape. Alternatively, a geometrical model of the full hand can be drawn in front of the target object showing directly the relationship between the object and the hand.

In another particular implementation, the feedback interface 35 can be implemented using some of the sensory substitution methods, such as electro- and/or vibrotactile stimulation or any other form of tactile stimulation or in general any other method for the sensory restoration (e.g., sound feedback). This implementation of the feedback interface can be used alone or in combination with the aforementioned AR feedback.

Methods Description

The method for the semi-automatic control of the ULD comprises several real time processing modules implementing a sequence of steps (see FIG. 4):

41: Data Acquisition module collects the data about the ULD state and 2D/3D structure of the environment from the sensors 31 and 32, respectively.

42: Artificial Perception module analyzes the structural data, identifies the target object and determines the properties of the target object that are relevant for implementing automatic reaching and grasping with the ULD.

43: Sensor Fusion module combines the outputs of the Artificial Perception module and the information about the ULD state to determine additional information for controlling automatic reaching and grasping.

44: Cognitive Processing module uses the outputs from the Artificial Perception and Sensor Fusion modules to autonomously decide appropriate strategies to reach for and grasp the target object.

45: ULD Control module sends commands to the ULD to implement the strategies selected by the Cognitive Processing module (automatic control) or to respond to the user commands (manual control).

46: User Feedback module receives the data about the ULD state (Data Acquisition), target object (Artificial Perception), and automatic operation of the system (Cognitive Processing) and based on this provides visual feedback (augmented reality) to the user.

47: User Command module detects and decodes user commands and intentions, and based on this, triggers the automatic control and/or directly commands the ULD (manual control).

The method steps can be processed by a computer program executed on a processor of the control unit 1 or the controller 33.

In one particular implementation, Artificial Perception module relies on the use of the state-of-the-art computer vision algorithms for analyzing 2D/3D imaging data, including for example various stereo processing methods and different clusterization, classification and feature extraction techniques. Some of the possible choices are Scale-Invariant Feature Transform (SIFT), Random Sample Consensus (RANSAC), Simultaneous Localization and Mapping (SLAM), and Kinect Fusion. The outcome of this processing is a geometrical model of the environment, including the objects that might be potential grasping targets. In the next step, one of the objects is selected as the target, and a geometrical model of the object is constructed in absolute or relative coordinates. The object model provides information about the physical object properties (e.g., shape and size).

In one particular implementation, Sensor Fusion module compares the geometrical object model and information about the configuration of the ULD to determine the relative orientation of the ULD gripper with respect to the object. It can employ prediction and filtering algorithms (e.g., adaptive Kalman Filtering) to estimate the absolute or relative pose of the user and/or prosthesis in 3D space.

In one particular implementation, Cognitive Processing module uses a set of rules to select an appropriate configuration and/or orientation of the ULD gripper from a predefined set of possible configurations and/or orientations. These rules map the information about the physical properties and/or pose of the target object to the appropriate preshape/orientation strategy, and they can be hand crafted or computer generated (machine learning). The rules can be explicit ("IF-THEN", fuzzy networks, inductive learning) or implicit (e.g., neural networks).

In another particular implementation, Cognitive Processing module determines the appropriate configuration/orientation of the ULD gripper from the continuous space of all physically possible configurations/orientations. The module also calculates the trajectory (i.e., a sequence of transient configurations/orientations) to be implemented in order for the ULD to attain the determined final configuration/orientation. This processing can be performed by using the methods of "visual servoing".

In one particular implementation, User Feedback module constructs graphical objects that should convey visual feedback to the user. Those objects are then projected to a wearable display device for the presentation to the user. This processing is based on the conventional computer vision methods (e.g., computer geometry and linear algebra).

In another particular implementation, the feedback is delivered through tactile stimulation and in this case the User Feedback module implements the mapping from the variables of interest to the corresponding haptic stimulation patterns. Any of the tested coding schemes available in the literature on sensory substitution or original coding algorithms designed specifically for this application can be implemented.

In one particular implementation, User Command module employs conventional myoelectric control. Muscle activity is recorded using electromyography (EMG) and simple triggering is employed to activate the autonomous control of ULD. To implement manual control overriding the automatic operation, proportional myoelectric control can be used. The position, velocity and/or grasping force of the ULD can be made directly proportional to the recorded muscle activity (electromyography). Muscle co-activation is used to change the control mode.

In another particular implementation, User Command module implements any of the state-of-the-art pattern recognition algorithms for myoelectric control, or some of the latest generation methods for simultaneous and proportional control of multi-degree of freedom ULD.

In yet another particular implementation, User Command module can rely on some less conventional man-machine interfaces (e.g., voice, brain-machine interfaces etc.)

EXAMPLE IMPLEMENTATIONS

Example 1 (Hand Prosthesis with an Active Imaging Device and Augmented Reality)

The user is equipped with the special glasses that are specifically designed for this application. The glasses have a see-through AR screens and miniature active imaging device embedded into the glass frames. The imaging device provides a 3D structure of the scene in front of the subject. All the components are small factor and they are integrated so that these specialized glasses look very much like ordinary glasses.

The subject is an amputee and uses a dexterous prosthetic hand with individually controllable fingers and active wrist joint allowing wrist flexion/extension and pronation/supination movements. The hand is instrumented with position and grasping force sensors, and also with inertial measurement units measuring the hand orientation in space. The sensors are embedded within the hand. The programmable semi-automatic controller is also embedded into the hand electronics.

The glasses are connected to the controller via a wireless link transmitting 3D information acquired from the imaging device to the controller and processed AR feedback information back to the glasses to be drawn at the see through displays.

Triggering of the automatic operation and manual control during semi-automatic operation are implemented using simple myoelectric interface comprising two channels of bipolar EMG.

Next, we present a hypothetical use case scenario. The user approaches the table with a set of objects. He/she looks at the one he would like to grasp and the system instantly provides visual feedback acknowledging that the object was recognized (e.g., the target object is marked). The subject reaches with the hand and at the same time triggers the hand to open by briefly contracting his extensor muscles. While the hand travels towards the object, the controller has already analyzed the 3D information obtained from the imaging device, segmented the target object and determined its properties (shape and size). As a result, it commands the hand to preshape into an appropriate grasp. Simultaneously, the controller continuously processes the inertial data estimating the orientation of the hand with respect to the target object. Based on this, it automatically controls the two degrees of freedom in the wrist joint so that the hand is properly oriented for the grasp. When the hand comes close to the object, the user triggers closing and grasps the object.

While holding, the user relies on manual control to manipulate the object and control grasping force. The user controls the force by relying on a simple AR feedback, a bar placed in the peripheral vision depicting the current grasping force.

Note that the automatically controlled reach and grasp movement, operates very similarly to the natural movement. The user expresses the high level goal (grasp the object) and triggers the system, and the "hand" implements the rest of the steps.

Example 2 (Hand Prosthesis with Augmented Reality)

The user of a hand prosthesis wears standard commercially available AR glasses (e.g., Google glass project). The glasses are wirelessly connected to the controller embedded within the hand, which is operated using a conventional two channel myocontrol interface.

Controller receives position and force data from the embedded prosthesis sensors and provides artificial proprioceptive and force feedback through AR. Specifically, an ellipsis is drawn in the peripheral visual field of the user by using AR glasses. The horizontal axis is made proportional to the current hand aperture and vertical axis is proportional to the grasping force. Therefore, the user receives information about the hand as the change in the shape of the ellipsis. This information is send by the controller to the glasses which project the image (ellipsis) to the user.

A hypothetical use case scenario could be as follows. The subject approaches the table with a set of objects. He/she starts reaching for the target object and simultaneously starts preshaping the hand. This is possible despite the fact that the subject in the moment he/she starts reaching does not see the hand. The subject however has the full information about the configuration of the hand through the virtue of the provided AR feedback. After the grasp is established, the subject controls the grasping force through the AR grasping force feedback.

Note that the reaching and grasping with this system simulates the sequence of events that is typical for the grasping of able bodied subjects. Namely, the amputee can start with the hand preshape while the hand is being transported to the target object, so that the hand is appropriately configured and ready for closing at the end of the reach.

Example 3 (Full Arm Prosthesis with an Active Imaging Device and Augmented Reality)

This implementation is very similar to the implementation presented in Example 1. The main difference is in the complexity of the prosthetic system. In this case, the subject is equipped with a full arm prosthesis which has an active shoulder, elbow and wrist joints and independently controllable fingers.

The use case scenario could look something like this. The user wants to grasp an object. He/she looks at the object and the system provides the acknowledgement that the object is recognized and selected as the target. The user triggers the system by providing a brief contraction using one of his functional muscles around the shoulder. The controller analyzes the 3D image of the scene and the target object and plans the reaching trajectory, orientation of the end effector (hand) and configuration of the end effector (hand) that are appropriate to reach for and grasp the object. The system then executes the plan, i.e., the arm is controlled in real time to reach and grasp the object.

Similarly as in the example one, this simulates the manner the same task is executed in able bodied subjects. The complex task of reaching and grasping in 3D space is implemented effortlessly for the user, i.e., he/she only focuses to the overall goal and triggers the system, while the system implements all the other steps fully automatically.

The invention claimed is:

1. A system for controlling a hand prosthesis comprising:
   electromyography (EMG) sensors configured to provide EMG signals from a user's muscles;
   a three dimensional (3D) scanning device configured to generate 3D data including depth information of a target viewed by the 3D-scanning device; and
   a control unit configured to receive signals from the EMG sensors and the 3D-scanning device, the control unit including:
   a myoelectric control module which processes recorded EMG signals and detects activity of the user's muscles,
   a controller receiving information about muscle activity from the myoelectric control module which drive state transitions within the controller to implement control logic,
   a computer imaging module configured to receive 3D data from the 3D-scanning device and reconstruct a 3D geometrical model of a scene which includes an object that is the target for grasping, and
   a hand control module configured to receive information from the computer imaging module and information about hand prosthesis orientation and generate a grasp type and an aperture size appropriate to grasp the object, the hand control module configured to send commands to the hand prosthesis to implement a desired strategy; and
   a feedback unit configured to receive information from the computer imaging module and providing feedback to the user.

2. The system for controlling a hand prosthesis according to claim 1, further comprising an inertial measurement unit attachable to the hand prosthesis which generates 3D position and orientation information of the prosthesis, the control unit further configured to receive the 3D position and orientation information of the prosthesis.

3. The system for controlling a hand prosthesis according to claim 1, wherein the EMG sensors are configured such that EMG signals are taken from finger flexor and extensor muscle groups of a user.

4. The system for controlling a hand prosthesis according to claim 1, further comprising an artificial limb to which the hand prosthesis is attached, wherein the EMG sensors are configured to obtain EMG signals from functional muscles around a shoulder of the user.

5. The system for controlling a hand prosthesis according to claim 1, wherein the feedback unit includes a visual output device outputting visual data showing positions of joints in the hand prosthesis.

6. The system for controlling a hand prosthesis according to claim 1, wherein the computer imaging module is also configured to receive sensor data from the hand prosthesis in the form of position and force data and use this data to augment the visual feedback to the user.

7. The system for controlling a hand prosthesis according to claim 1, further comprising a stereo vision device configured as Augmented Reality (AR) glasses wearable by a user and controlled by the computer imaging module to display a 3D picture of a scene in front of the user.

8. The system for controlling a hand prosthesis according to claim 7, wherein the computer vision module is configured to output a marking signal in a video stream based upon an automatic selection by the control unit of an object which is to be grasped, the marking signal marking the selected object in the 3D picture of the scene in front of the user.

9. The system for controlling a hand prosthesis according to claim 1, wherein processing in the control unit is organized in a sequential manner and the modules are activated (triggered) by a finite state machine.

10. The system for controlling a hand prosthesis according to claim 1, wherein the 3D-scanning device is selected from the group consisting of a stereovision camera device, a laser scanning device, a radar device, and a white-light scanning device.

* * * * *